United States Patent
Addison et al.

(10) Patent No.: US 10,716,503 B2
(45) Date of Patent: *Jul. 21, 2020

(54) PAIN LEVEL DETECTION AND CHARACTERIZATION USING CAPACITIVE SENSORS

(71) Applicant: Covidien LP, Mansfield, MA (US)

(72) Inventors: Paul S. Addison, Edinburgh (GB); James N. Watson, Edinburgh (GB); Eric Morland, Erie, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/121,436

(22) Filed: Sep. 4, 2018

(65) Prior Publication Data
US 2018/0368761 A1 Dec. 27, 2018

Related U.S. Application Data

(63) Continuation of application No. 14/996,453, filed on Jan. 15, 2016, now Pat. No. 10,076,277.

(60) Provisional application No. 62/106,509, filed on Jan. 22, 2015.

(51) Int. Cl.
| | | |
|---|---|---|
| A61B 5/04 | (2006.01) |
| A61B 5/00 | (2006.01) |
| A61B 5/0476 | (2006.01) |
| A61B 5/053 | (2006.01) |
| A61B 5/1455 | (2006.01) |

(52) U.S. Cl.
CPC .......... *A61B 5/4824* (2013.01); *A61B 5/4821* (2013.01); *A61B 5/0476* (2013.01); *A61B 5/053* (2013.01); *A61B 5/14551* (2013.01)

(58) Field of Classification Search
CPC ..... A61B 5/0476; A61B 5/053; A61B 5/0531; A61B 5/4824
See application file for complete search history.

(56) References Cited

U.S. PATENT DOCUMENTS

| | | | |
|---|---|---|---|
| 10,076,277 B2 * | 9/2018 | Addison | A61B 5/4824 |
| 2003/0236487 A1 * | 12/2003 | Knowlton | A61B 18/1402 604/20 |

* cited by examiner

*Primary Examiner* — Eric D. Bertram

(57) ABSTRACT

Systems, methods, sensors, and software for providing enhanced measurement and detection of patient pain response are provided herein. In a first example, a measurement system is provided that includes a capacitive system configured to measure a capacitance signal of tissue of the patient using a capacitive sensor applied to the tissue of the patient. The measurement system also includes a patient monitor configured to measure an electrical signal representing brain activity of the patient using a brain activity sensor applied to the tissue of the patient. The measurement system also includes a processing system configured to determine pain metrics based at least on the capacitance signal and the electrical signal, and determine a pain response of the patient based at least on the pain metrics and pain calibration information for the patient.

20 Claims, 8 Drawing Sheets

PAIN LEVEL DETECTION AND CHARACTERIZATION USING CAPACITIVE SENSORS

RELATED APPLICATIONS

This application hereby claims the benefit of priority to U.S. patent application Ser. No. 14/996,453, titled "PAIN LEVEL DETECTION AND CHARACTERIZATION USING CAPACITIVE SENSORS," filed Jan. 15, 2016, which claims priority to U.S. Provisional Patent Application 62/106,509, filed Jan. 22, 2015, which are hereby incorporated by reference in their entirety.

TECHNICAL FIELD

Aspects of this disclosure are related to the field of physiological sensing of pain, and in particular, sensors and associated systems for pain level detection of patients.

BACKGROUND

Various medical devices can non-invasively measure physiological parameters of a patient. Some of these devices include pulse oximetry devices and electroencephalogram (EEG) measurement devices, among others. An example is the BIS™ brain monitoring system from Covidien LP (Boulder, Colo.). These devices can measure pulse, breathing rates, brain activity, or other parameters experienced by the patient during various medical procedures, such as surgery and subsequent recovery.

Patient pain levels during sedation can be difficult to quantify and measure due to the subjective nature of pain, as well as due to a consciousness level of the patient. In some medical procedures the patient receives anesthesia or other conscious pain reduction treatments, which can include unconsciousness, amnesia, analgesia, and muscle relaxation, which make quantification and measurement of pain levels difficult. Furthermore, patient-to-patient variation in pain response and the possibility of subjectivity in nociception pain response measurements make pain response measurements difficult.

Some physiological measurement techniques, such as EEG measurements, can provide an indication of a current level of brain activity, and corresponding depth of anesthesia, experienced by a patient, but do not identify a pain response of that patient. Capacitive sensing has been employed to measure some physiological parameters by applying electric fields to the tissue of the patient. However, this capacitive sensing merely measures parameters such as pulse rate of a patient for blood perfusion and oxygen saturation measurements.

Overview

Systems, methods, sensors, and software for providing enhanced measurement and detection of patient pain response are provided herein. In a first example, a measurement system is provided that includes a capacitive system configured to measure a capacitance signal for tissue of the patient. The measurement system also includes a patient monitor configured to measure an electrical signal representing brain activity of the patient. The measurement system also includes a processing system configured to determine pain metrics based at least on the capacitance signal and the electrical signal, and determine a pain response of the patient based at least on the pain metrics and pain calibration information for the patient.

In a second example, a method of operating a measurement system to detect pain response in a patient is provided. The method includes measuring a capacitance signal of tissue of the patient using a capacitive sensor proximate to the tissue of the patient, measuring an electrical signal representing brain activity of the patient, and determining a pain response of the patient based at least in part on pain metrics derived from the capacitance signal, the electrical signal, and pain calibration information for the patient.

In a third example, an apparatus is provided. The apparatus includes one or more computer readable storage media, and program instructions stored on the one or more computer readable storage media for at least identifying a pain response in a patient. When executed by a processing system, direct the processing system to at least monitor a capacitance signal of tissue of the patient using at least one capacitor element applied to the tissue of the patient, process the capacitance signal to derive one or more capacitive pain metrics for the patient, identify an electrical signal representing brain activity of the patient, and determine the pain response of the patient based at least on correlating the electrical signal to the capacitive pain metrics.

DETAILED DESCRIPTION

The examples discussed herein include systems, apparatuses, methods, and software for enhanced measurement of pain metrics in patients and enhanced detection of pain response in patients. Some physiological measurement techniques, such as ECG/EEG, can provide a measure of a current level of anesthesia experienced by a patient based in part on brain activity or electrical activity in tissue of a patient. In the examples herein, capacitive sensing using one or more capacitor plates positioned in proximity to tissue of a patient is included with other physiological measurement techniques to identify pain metrics of a patient. These pain metrics can be used for characterization of various levels of pain response of the patient, even when the patient is not conscious. This characterization of patient pain response is a further indicator of the depth of anesthesia of the patient and can be used to maintain a desired depth of anesthesia to prevent patient awareness during a painful event such as surgery.

Figure 1:
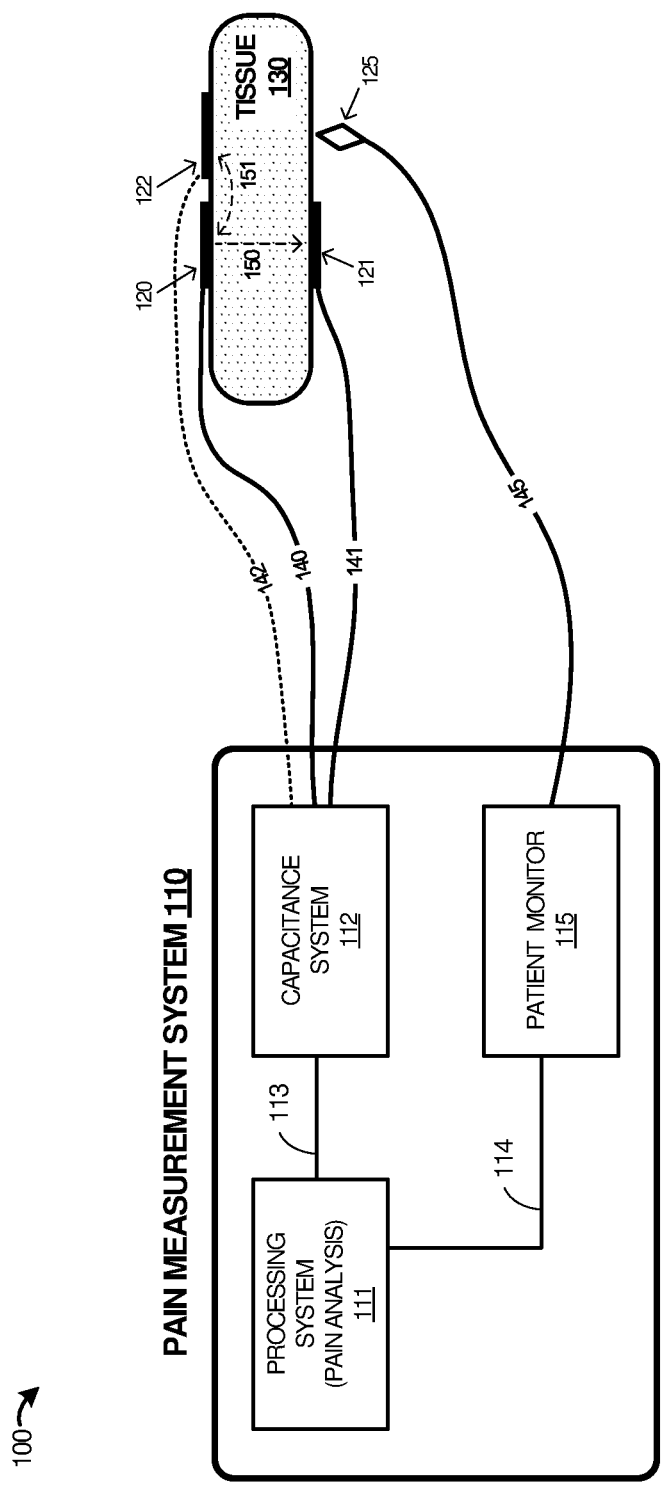
FIG. 1 is a system diagram illustrating a physiological measurement system.

As a first example of a measurement system for monitoring physiological parameters of a patient, FIG. 1 is presented. FIG. 1 is a system diagram illustrating physiological measurement system 100. System 100 includes pain measurement system 110, capacitive elements 120-122, sensor element 125, and tissue 130. In operation, capacitive elements 120-122 and sensor element 125 are configured to monitor various properties of tissue 130, and signals representative of these properties are provided to pain measurement system 110 for processing and analysis.

Pain measurement system 110 includes processing system 111, capacitance system 112, and patient monitor 115. In some examples, patient monitor 115 is included in other equipment than pain measurement system 110, and signals detected by patient monitor 115 are provided to pain measurement system 110. Processing system 111 and capacitance system 112 communicate over link 113. Patient monitor 115 and processing system 111 communicate over link 114. Links 113 and 114 can each comprise one or more analog or digital links.

Turning first to the capacitive sensing elements of FIG. 1, capacitance system 112 monitors physiological signals associated with tissue 130 using ones of capacitive elements 120-122. For example, capacitance system 112 can drive electrical signals over links 140-142 and detect changes in those electrical signals to monitor tissue 130. Capacitance system 112 can drive an oscillating or alternating current (AC) signal onto any of links 140-142 for emission by capacitive elements 120-122 proximate to tissue 130. Capacitance system 112 detects changes in signals driven onto links 140-142 which correspond to capacitance value changes. Signals, data, or information related to the capacitance parameters measured by capacitance system 112 are provided to processing system 111 over link 113 for pain analysis.

Various capacitive arrangements can be employed, using one or more capacitive plates of capacitive elements 120-122. Capacitive element 121 or 122 can be omitted for measurement, depending upon the capacitive arrangement employed. In a first example arrangement, capacitive elements 120-121 are positioned on opposite sides of tissue 130 and used as two individual single-plate capacitors in a differential measurement arrangement which each emit an electric field into tissue 130 from opposite sides of tissue 130. In a second example arrangement, capacitive elements 120-121 are positioned on opposite sides of tissue 130 and used as capacitive plates in a two-plate capacitor with tissue 130 as a dielectric material between the two plates. In a third example arrangement, one or both of capacitive element 120 and capacitive element 122 are positioned on the same side of tissue 130 with a fringe field detection arrangement employed.

In addition to the capacitive sensing elements of FIG. 1, further physiological measurements can be performed. Specifically, patient monitor 115 and sensor element 125 are configured to measure one or more parameters of tissue 130 or the patient associated with tissue 130. However, patient monitor 115 and sensor element 125 may be omitted in some examples. It should be understood that sensor element 125 is representative of any number of sensor elements that are positioned onto tissue 130 or in proximity to a patient. In a first example, patient monitor 115 comprises an optical sensing system, such as a pulse oximeter, which can measure pulse, breathing, blood parameters, or other information using at least sensor element 125. In a second example, patient monitor 115 comprises a patient monitor that measures electrical signals representing brain activity of the patient which can characterize or measure a depth of anesthesia applied to the patient. Further patient monitoring systems can be employed, such as a composite variability index (CVI) monitor, electroencephalography (EEG) monitor, electrocardiography (ECG) monitor, electromyography (EMG) monitor, plethysmography (PPG) monitor, blood pressure monitor, heart rate monitor, breathing monitor, pulse monitor, or other patient monitoring systems, including variations and combinations thereof. Signals, data, or information related to the parameters measured by patient monitor 115 are provided to processing system 111 over link 114 for pain analysis.

Figure 2:
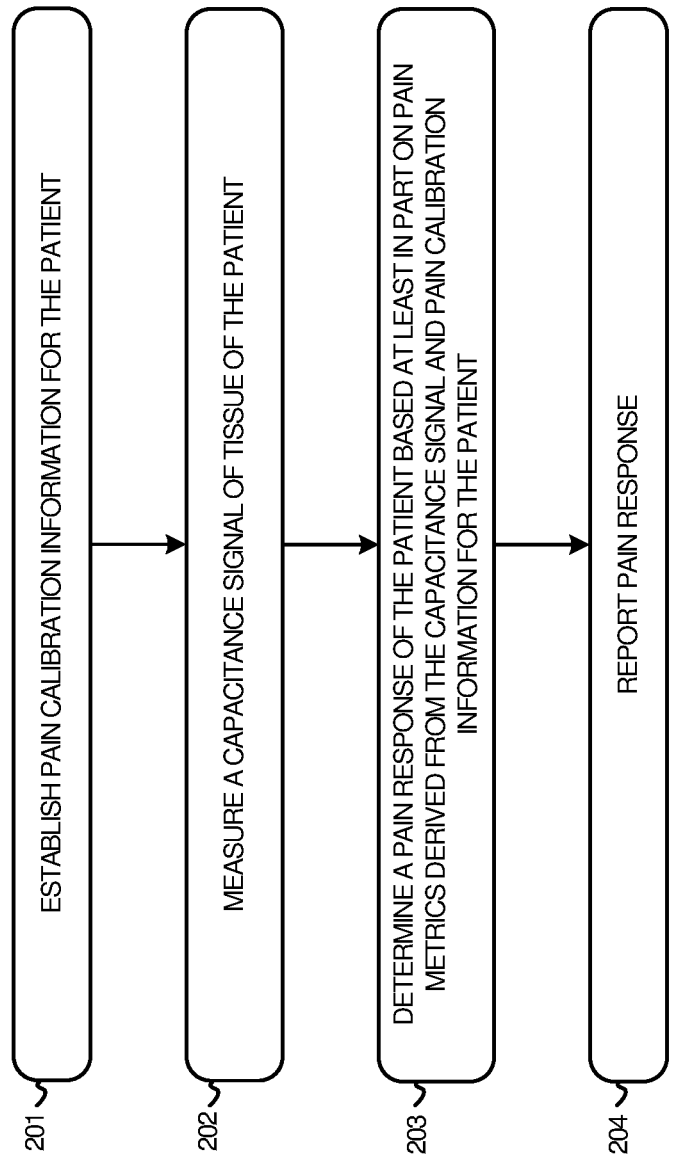
FIG. 2 is a flow diagram illustrating a method of operating a pain measurement system.

FIG. 2 is provided to further illustrate the operation of the elements of FIG. 1. FIG. 2 is a flow diagram illustrating a method of operating pain measurement system 110. The operations of FIG. 2 are referenced below parenthetically. In FIG. 2, processing system 111 establishes (201) pain calibration information for the patient. This pain calibration information comprises calibration information that relates capacitance measurements for the patient to various pain levels or pain metrics for the patient.

In some examples, a pain calibration test is performed prior to monitoring pain metrics for a patient to establish baseline response levels for the patient. This pain calibration test can include performing one or more calibration stimuli to the patient while the patient is conscious and responding, such as a pinch, poke, or other contact during which a capacitance signal is monitored using capacitance system 112 to observe and analyze a physiological reaction to the stimuli. This physiological reaction to the pain calibration test can be used to establish one or more pain response thresholds for various monitored signals associated with capacitance system 112 and capacitance elements 120-122. The pain calibration test can also be performed to establish pain calibration information for patient monitor 115. In further examples, a pain calibration test is omitted and pain calibration data is employed from previously performed pain calibration tests or from standardized pain calibration data.

Capacitance system 112 measures (202) a capacitance signal of tissue 130 of the patient. The capacitance signal can change over time due to changes in properties of tissue 130 from normal physiological processes as well as from pain responses of the patient. The capacitance signal can comprise various signals associated with application of an electric field onto tissue 130 by any of capacitance elements 120-122. For example, a capacitance value of one or more of capacitor plates of capacitance elements 120-122 can be monitored. When a capacitance value is monitored, a current draw of any of capacitance elements 120-122 can change over time and this current draw can be converted into a capacitance value for an associated capacitor plate of capacitance elements 120-122 or a capacitor formed by ones of capacitance elements 120-122. Other methods to monitor capacitance signals associated with any of capacitance elements 120-122 can be employed.

From these capacitance signals, various pain metrics can be identified. In FIG. 2, processing system 111 determines (203) a pain response of the patient based at least in part on pain metrics derived from the capacitance signal and the pain calibration information for the patient. Pain metrics can indicate that a patient is experiencing a measure of pain, which can vary on the particular metrics involved. Also, pain metrics can be dynamic where changes in various metrics correspond to changes in a pain response. The metrics comprise indicators for pain response for a patient, which in these examples are based on various physiological signals monitored using at least capacitance elements 120-122. For example, a change in capacitance signals monitored for capacitance elements 120-122 rate can indicate a change in a level of pain for a patient.

Capacitance measured using capacitance elements 120-122 can vary based on physical properties of the tissue, including properties that may be associated with a pain response in the patient. Examples of these properties of the tissue include moisture levels, movement, vasoconstriction, dielectric changes, or other changes of tissue 130 or the patient. Rising or falling values of the capacitance, such as direct current (DC) trends in the capacitance signal, can be used to indicate the changes in these tissue properties, which may indicate that the patient is having a pain response. Dynamic changes, such as AC frequency content changes of the capacitance, can also be used to identify a pain response. These various changes in the capacitive signal, such as DC trends or AC frequency content changes, may be referred to as pain metrics. Further factors that involve the capacitance signal can be used to determine pain metrics, such as correlations to other signals, such as those monitored by patient monitor 115. Pain calibration processes, such as described herein, can be employed to qualify the DC trends or AC frequency content changes as being related to pain response of the patient, and exclude the DC trends or AC frequency content changes as being noise or other environmental factors unrelated to pain response. Correlations and further examples are discussed below in FIGS. 3-7.

Once the pain response has been identified, pain measurement system 110 reports (204) the pain response. Pain measurement system 110 can include various user interface elements, displays, indicator lights, speakers, or other user interface equipment. These user interface elements can be included in processing system 111 or in other portions of pain measurement system 110. In some examples, pain measurement system 110 reports pain response information over a network interface to further systems and equipment.

The pain response can be normalized to the pain calibration information for the patient identified in operation 201. Also, various thresholds can be established for the pain metrics based on the pain calibration information, and reporting of the pain response can be modified based on the thresholds. Individual thresholds can be established for the various parameters or signals monitored.

Figure 3:
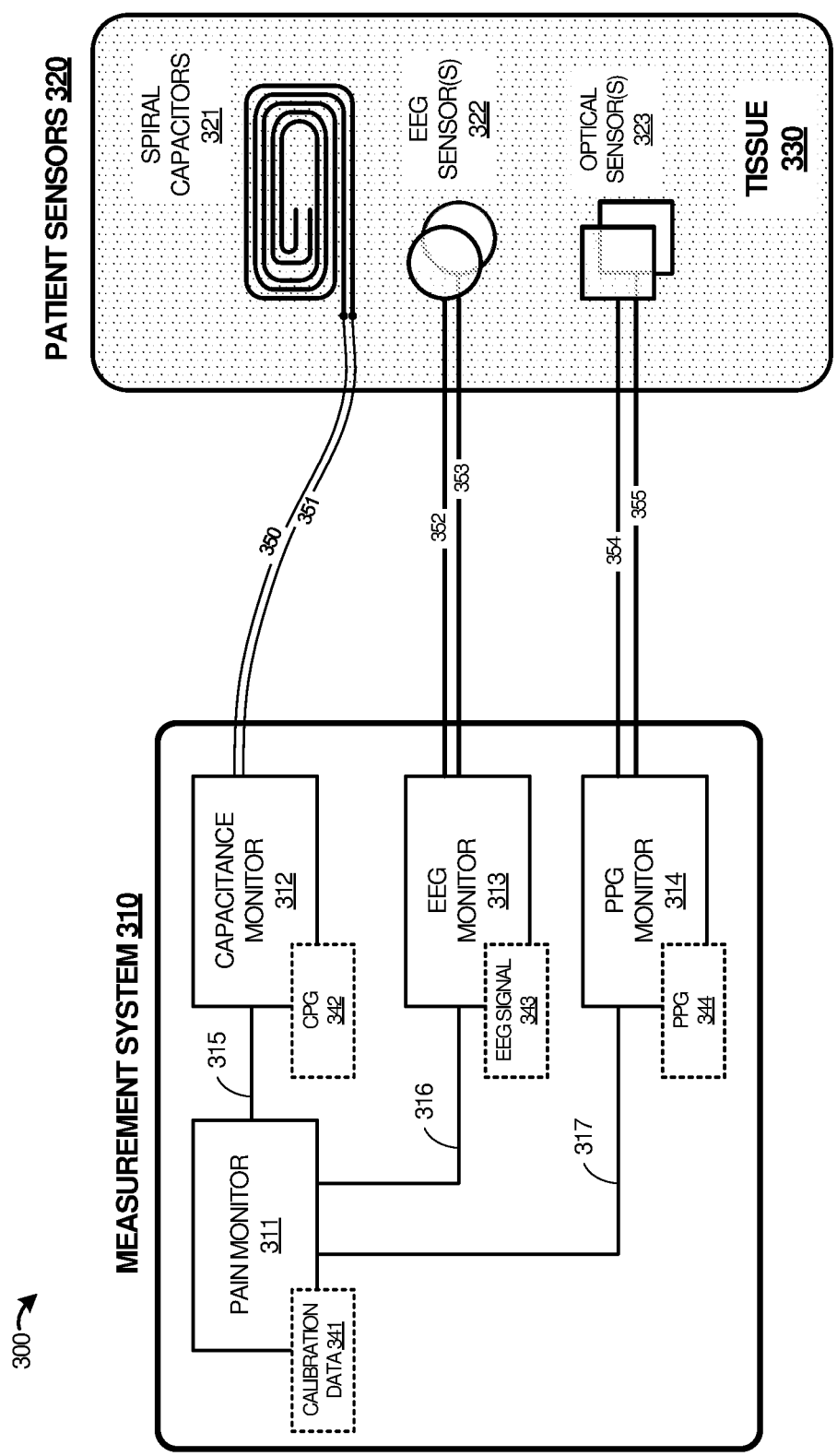
FIG. 3 is a system diagram illustrating a physiological measurement system.

As a second example of a pain monitoring and reporting system, FIG. 3 is presented. FIG. 3 is a system diagram illustrating physiological measurement system 300. FIG. 3 includes measurement system 310, patient sensors 320, and tissue 330. In operation, sensor elements 321-323 are configured to monitor various properties of tissue 330, and signals representative of these properties are monitored by measurement system 310 for processing and analysis.

Measurement system 310 includes processing system pain monitor 311, capacitance monitor 312, EEG monitor 313, and photoplethysmogram (PPG) monitor 314. In some examples, capacitance monitor 312, EEG monitor 313, or PPG monitor 314 are included in other equipment than measurement system 310, and signals detected by capacitance monitor 312, EEG monitor 313, PPG monitor 314 are provided to pain measurement system 310. In other examples, ones of capacitance monitor 312, EEG monitor 313, or PPG monitor 314 are omitted, or included in pain monitor 311. Pain monitor 311 and capacitance monitor 312 communicate over link 315. Pain monitor 311 and EEG monitor 313 communicate over link 316. Pain monitor 311 and PPG monitor communicate over link 317. Links 315, 316, and 317 can each comprise one or more analog or digital links.

Turning first to the capacitive sensing elements of FIG. 3, instead of plate capacitors for monitoring tissue 330, one or two spiral capacitor plates 321 are employed, and communicate with capacitance monitor 312 over measurement links 350-351. Spiral capacitors 321 comprise wires, printed circuit traces, flex circuit traces, cut or stamped foil, or other conductive materials. Spiral capacitors 321 are concentric spirals in this example which form closely spaced capacitor plates. Capacitive sensing is performed by capacitance monitor 312 using one or both of spiral capacitors 321. When a single one or spiral capacitors 321 is used, then the single plate is employed as a single-plate capacitor which uses fringe fields to sense changes in tissue 330 and the environment proximate to the single-plate capacitor. When both of spiral capacitors 321 are used, the capacitor plates of spiral capacitors 321 can be employed as a two-plate capacitor which uses fringe fields that extend between both capacitor plates to sense changes in capacitance. When the two-plate capacitor configuration is used, changes in observed capacitance signals are highly coupled to changes in the immediate environment of spiral capacitors 321, due in part to the tight spacing between the elements of spiral capacitors 321. Thus, as a high correspondence to changes related to tissue 330 can be established instead of external interferences. In other examples, each of the spiral capacitor plates in spiral capacitors 321 can be employed individually as single-plate capacitors, or in a differential capacitor arrangement.

EEG sensors 322 can measure various electrical properties of tissue 330 and the associated patient, and communicate with EEG monitor 313 over measurement links 352-353. Data measured by EEG sensors 322 are monitored by EEG monitor 313 for establishment of one or more indices of patient consciousness levels or depth of anesthesia applied to the patient based on electrical signals representing brain activity of the patient. In some examples, EEG monitor 313 identifies a bispectral index, or BIS, that can provide a measure of a current level of anesthesia experienced by a patient. In other examples, EEG monitor 313 can identify a composite variability index, or CVI, that can be used to provide a measure of a current level of nociception in a patient. Nociception comprises pain receptor responses in patients.

Optical sensors 323 are employed to measure optical properties of tissue 330, and communicate with PPG monitor 314 over measurement links 354-355. In some examples, optical sensors 323 comprise optical emitters and detectors which can emit and detect light signals through tissue 330 for identifying various properties of tissue 330. For example, PPG monitor 314 can monitor an optically derived plethysmogram (PPG) of tissue 330, or can also determine a pulse rate, heart rate, breathing rate, oxygen saturation of the blood of tissue 330, hemoglobin properties of tissue 330, among other properties, using optical sensors 323.

Pain monitor 311 comprises processing circuitry, computer-readable storage media, communication interfaces, and user interface equipment. The user interface equipment is configured to present pain response indications to an operator, such as using a display, indicators, or graphical user interface elements. The processing circuitry comprises microprocessor or microcontroller equipment and is configured to read and execute instructions from the computer-readable storage media for operating as discussed herein, such as in FIG. 4 below, to identify pain metrics, apply pain calibration information to establish pain thresholds, and report pain responses. The communication interfaces, such as transceivers, network interface equipment, and the like, are configured to receive data from the monitoring systems of measurement system 310 and control the operations of the monitoring equipment during measurement of patient data.

Figure 4:
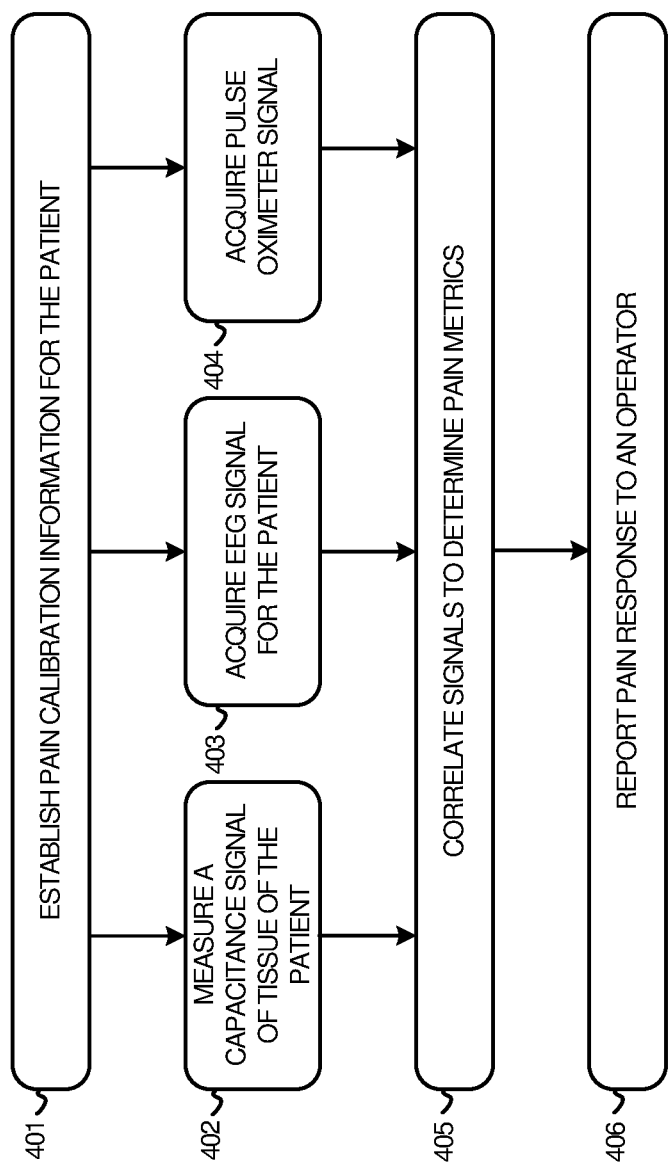
FIG. 4 is a flow diagram illustrating a method of operating a pain measurement system.

FIG. 4 is provided to further illustrate the operation of the elements of FIG. 3. FIG. 4 is a flow diagram illustrating a method of operating measurement system 310. The operations of FIG. 4 are referenced below parenthetically. In FIG. 4, measurement system 310 establishes (401) pain calibration information for the patient. In some examples, pain monitor 311 determines calibration data 341 from one or more calibration measurements of the patient, or retrieves calibration data 341 from previously performed calibration operations, such as predetermined calibration data or thresholds for the patient. This pain calibration data can relate physiological measurements for the patient to various pain levels or pain metrics for the patient.

A pain calibration test can be performed to establish calibrated pain response levels for the patient. This pain calibration test can include performing one or more calibration stimuli to the patient, such as a pinch, poke, or other contact during which physiological signals are monitored using capacitance monitor 312, EEG monitor 313, or PPG monitor 314 to observe and analyze a reaction to the stimuli. This reaction to the pain calibration test can be used to establish one or more pain response thresholds for various monitored signals associated with capacitance monitor 312, EEG monitor 313, PPG monitor 314, and associated sensing elements. In other examples, pain calibration data is imported from previously performed pain calibration tests or from standardized pain calibration data.

Capacitance monitor 312 measures (402) capacitance signals of tissue 330. The capacitance signals are monitored using one or more of spiral capacitors 321 applied to tissue 330. Capacitance monitor 312 provides an AC signal over associated links 350-351 which energize spiral capacitors 321 to emit an electric field into tissue 330. This electric field is related to current capacitance values for spiral capacitors 321, which can change over time due to changes in properties of tissue 330 from normal physiological processes as well as from pain responses of the patient. The capacitance value of one or more of spiral capacitors 321 can be monitored over time. Various methods to monitor capacitance signals associated with spiral capacitors 321 can be employed, such as current draw monitoring.

Based on the capacitance signals, capacitance monitor 312 determines a capacitive plethysmogram, namely CPG 342. A capacitive plethysmogram includes some similar features to a photoplethysmogram, but is measured with a capacitive sensor and can also include different signal components than a PPG. CPG 342 varies over time due to normal biological processes of the patient, such as pulse and breathing, but also in response to pain stimuli experienced by the patient and motion of the patient. Typically, motion of the patient or motion of tissue 330 corresponds to fast oscillations in the capacitance signals, changes in conductivity properties of tissue 330 due to moisture changes correspond to slow oscillation or DC shifts, and pulsatile signals correspond to periodic oscillations.

Signal components in CPG 342 that indicate pulse of the patient are typically caused by changes in arterial blood volume (due to pulsatile dielectric changes of tissue 330) as well as to pulsatile area/positional changes. An amplitude of CPG 342 changes relative to the amount of baseline capacitance for spiral capacitors 321. A patient experiencing pain may move or twitch causing somewhat rapid changes of motion which is also indicated in CPG 342. Capacitance is typically more responsive to motion and to moisture than optical sensors, so CPG 342 provides a different set of signal components and different signal amplitudes for signal components than what is monitored by optical sensors 323 and in PPG 344 as determined by PPG monitor 314 in operation 404.

EEG monitor 313 acquires an EEG (403) signal for the patient. In this example, an index or changing scalar value can be established by EEG monitor 313 by monitoring tissue 330 using EEG sensors 322, or other sensors, that indicates a level of anesthesia applied to the patient. This level of anesthesia can be monitored during a surgical procedure and used in conjunction with other indicators for anesthesia or consciousness, include ECG/EKG monitors, judgment of human personnel, or other factors. EEG monitor 313 provides EEG signal 343 to pain monitor 311 over link 316. Additionally, EEG monitor 313 can indicate a level of nociception pain response in the patient.

PPG monitor 314 acquires (404) a pulse oximeter signal for tissue 330 as PPG 344. PPG 344 indicates a waveform of the pulse of the patient, as measured by optical sensors 323 and PPG monitor 314. PPG monitor 314 provides PPG 344 to pain monitor 311 over link 317. PPG 344 can be used to identify a pulse rate, breathing rate, measures of blood oxygen concentrations, or other physiological metrics for the patient.

Pain monitor 311 correlates (405) the measured signals to determine pain metrics. These signals include CPG 342, EEG signal 343, and PPG 344, among any other measured signals that pain monitor 311 might obtain for the patient. The pain metrics can be derived from the various signals, and can include breathing/respiration rate, pulse rate, skin moisture/perspiration levels, and vasoconstriction levels, among other metrics. Correlation between the measured signals can include correlating signal components of CPG 342 to signal components of PPG 344 to identify physiological metrics for the patient that correspond to one another in time or in frequency. EEG signal 343 can provide additional information to correlate to changes in CPG 342 or PPG 344, such as using EEG signal 343 as a scaling factor for signal components of CPG 342 or PPG 344, or using EEG signal 343 as a factor in pain threshold establishment for the patient based on a current level of anesthesia.

Pain monitor 311 can correlate a pulse rate or respiration rate in CPG 342 to a pulse rate or respiration rate indicated by PPG 344. Changes in these rates can then be monitored over time for both CPG 342 and PPG 344 to identify a pain response. These correlations can ensure robustness in pain metric identification, such as in cases where a pain response is noted in both CPG 342 and PPG 344. For example, CPG 342 can be monitored against changes in a pulse rate or changes in a respiration rate which are monitored by PPG 344.

A "PMOD," or percentage modulation, of the various signals monitored for the patient can also be determined as a metric of pain response in the patient. PMOD comprises oscillation amplitude relative to the baseline amplitude for a particular signal. The oscillation amplitude is calculated by taking the maximum amplitude minus the minimum amplitude of CPG 342, and baseline amplitude, or DC bias, is calculated by taking the mean amplitude of CPG 342. In another example, changes in an AC amplitude of CPG 342 compared to a DC bias of CPG 342 can indicate the PMOD for CPG 342. PMOD can be represented by a percentage value. Changes in the PMOD for CPG 342 is typically more sensitive to pain metrics than PPG 344.

In pulse oximetry applications, such as used to identify PPG 344, a low PMOD can indicate that the pulse has a small amplitude relative to the amount of baseline optical energy hitting an associated optical detector. This PMOD analysis is usually performed pulse-by-pulse, and can be used to quantify a quality of the optically measured signal. For example, if PMOD is low, generally it might indicate vasoconstriction or low perfusion due to less blood flow and a smaller corresponding pulse amplitude. Conversely, a change to a higher-than-normal PMOD can indicate that bulk motion of the patient is occurring due to higher observed oscillation amplitudes than when stationary.

However, in capacitive measurements, these PMOD changes can indicate a pain response of the patient. Capacitive measurements, such as those performed to obtain CPG 342, are sensitive to changes in conductivity or dielectric of tissue 330. These changes in conductivity or dielectric can be correlated to a pain response of the patient. Moreover, if an optical PMOD of the patient indicates vasoconstriction while a capacitive PMOD indicates an increase in conductivity of tissue due to perspiration, then a pain response can be identified as occurring in the patient. If the vasoconstriction indicated by the optical PMOD does not occur concurrent with the capacitive PMOD change, then a pain response can be identified as not occurring since the vasoconstriction is not correlated to a conductivity change. An optical indication of vasoconstriction might occur due to various non-pain related factors, such as drug response, optical sensor movement or misalignment, blood loss, among other factors. By correlating metrics optically derived, such as vasoconstriction, with metrics capacitively derived, such as tissue conductivity, pain response can be identified in the patient and false pain response can be avoided.

Pulse rate of the patient can increase when the patient is experiencing pain, and this pulse rate can be identified in both PPG 344 and CPG 342. The patient may also perspire when experiencing pain or when highly stressed, and increasing moisture levels on the tissue under measurement can increase a baseline DC capacitance for a capacitive sensor. For perspiration, DC levels typically increase without corresponding changes to the AC pulsatile portions. In addition, vasoconstriction changes can occur due to pain. Vasoconstriction can leads to lower CPG pulse amplitudes, similar to found in a PPG signal, and these vasoconstriction changes can be indicated by a lower PMOD.

In another example, if a DC shift in PPG 344 correlates to a DC shift in CPG 342 during a predetermined depth of anesthesia indicated by a certain EEG level, then a pain response can be identified. Weighted metrics can be identified to produce a pain index for the patient based on the EEG level, where higher index numbers can indicate higher weights for various capacitive and optical pain metrics due to the deeper level of anesthesia experienced by the patient. For deeper levels of anesthesia, a lower pain response might be indicated by the capacitive and optical pain metrics due to a higher level of analgesia applied to the patient. However, a standardized pain response might be desired no matter the level of anesthesia and thus the various signals can be weighted or qualified based on the EEG. Other weightings and correlations to the EEG can be established.

In further examples, correlations between AC and DC levels of various measured signals, such as AC and DC levels of CPG 342, EEG signal 343, PPG 344, or other EEG data can be correlated to identify the pain response. Correlation between AC and DC levels of the various measured signals can include time domain and frequency domain correlations. In time domain correlations, various changes over time might be correlated. In frequency domain correlations, various frequency components of the monitored signals can be correlated in frequency and energy/amplitude.

Figure 5:
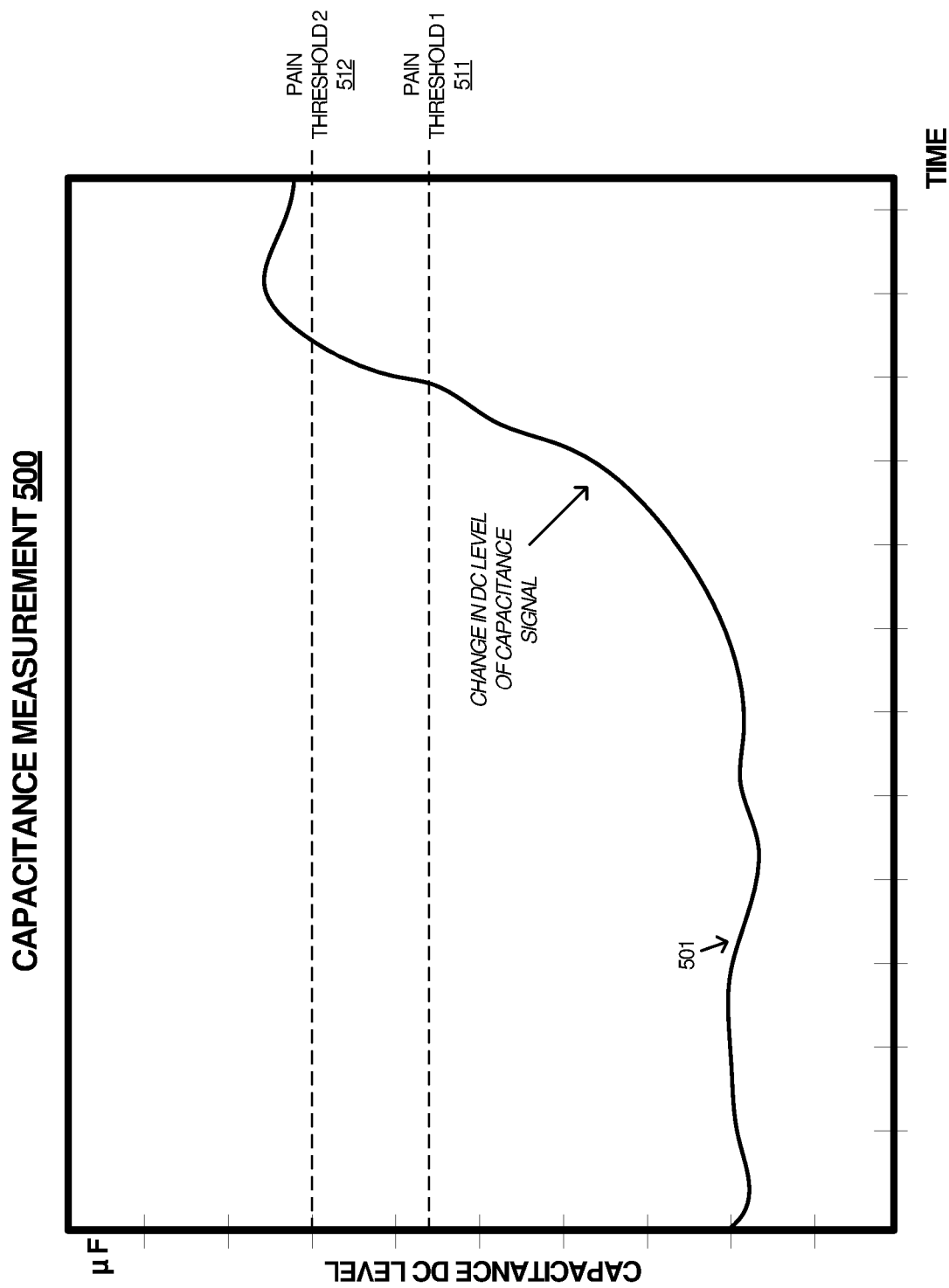
FIG. 5 illustrates measured physiological data for a patient related to pain response.

As a first example using DC level changes, FIG. 5 is presented. FIG. 5 is a capacitance measurement graph 500 indicating DC levels of a capacitance signal, such as a DC bias of CPG 342 with units of microfarads. CPG 342 can be processed by a low-pass filter to identify a DC level of CPG 342 over time and eliminate AC content above a predetermined frequency. This DC level can be monitored by pain monitor 311. DC level curve 501 indicates that the DC level of the capacitance signal increases over time, which can indicate a shift in the DC level of a measured capacitance of a capacitor sensor on tissue of a patient. This DC shift can occur due to changes in conductivity due to perspiration responsive to pain experienced by the patient.

To prevent false pain indications or to normalize the DC levels of the capacitance signal to calibration data for the patient, various thresholds can be established for the capacitance measurement. Pain threshold 1 (511) and pain threshold 2 (512) are shown in FIG. 5 which indicate a DC level that must be exceeded before an action is taken regarding pain reporting. For example, when pain threshold 1 is reached or exceeded then a first action can be taken, and when pain threshold 2 is reached or exceeded, then a second action can be taken. The first action might be indicating a first level of pain to an operator or health care professional, while the second action might be sounding an alarm or a more urgent indicator of pain. In another example, pain threshold 1 might indicate to pain monitor 311 to correlate a first set of metrics to a CPG signal, while pain threshold 2 might indicate to pain monitor 311 to correlate a second set of metrics to the CPG signal. These thresholds can vary based on the patient calibration data, whether measured with a calibration test or predetermined from previously obtained data or standardized patient data. These thresholds can also vary based on the current EEG signal for the patient, where at different levels of anesthesia can move the thresholds up or down based on an expected level of pain experienced by the patient, such as due to varying levels of induced analgesia in the patient.

Figure 6:
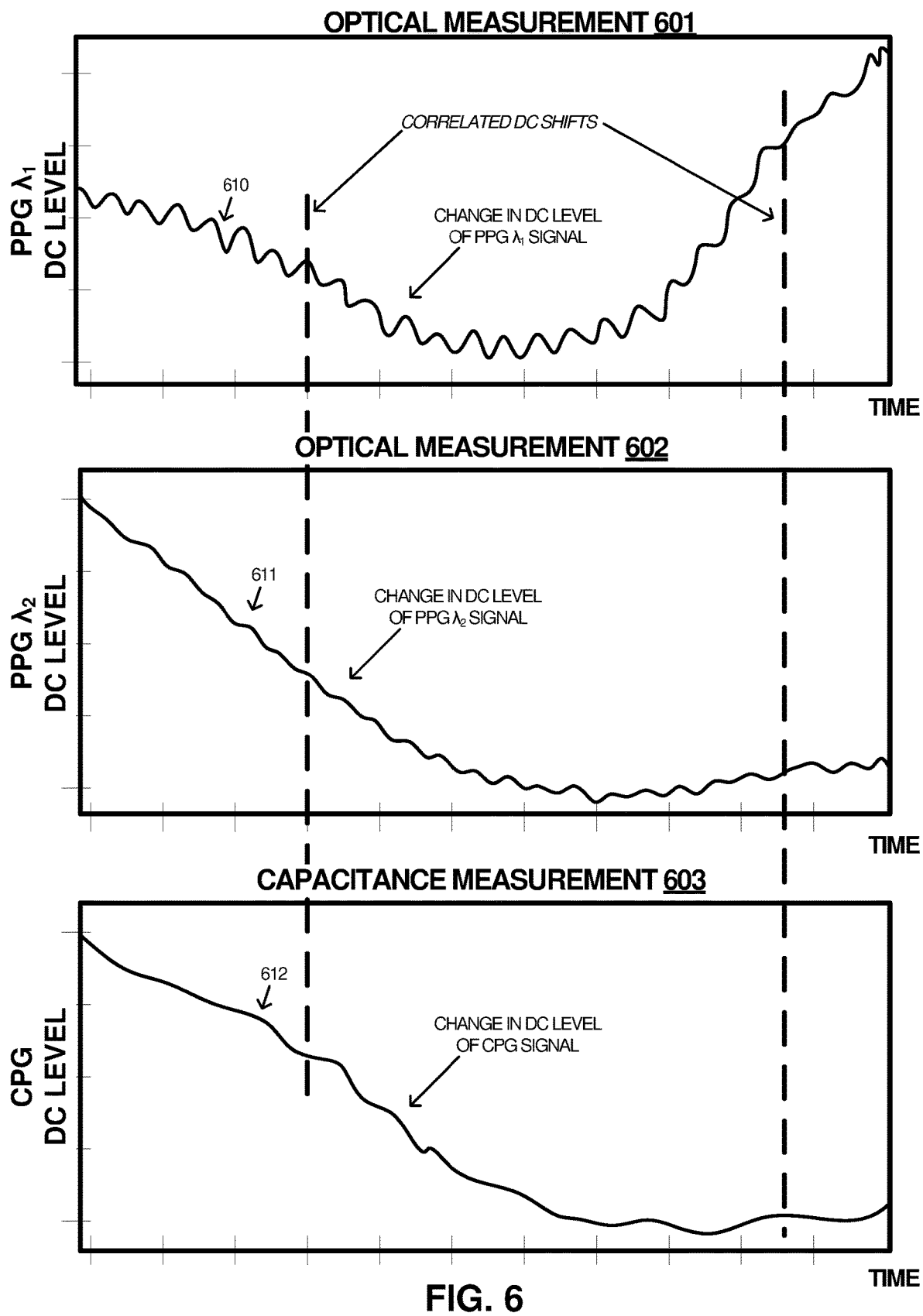
FIG. 6 illustrates measured physiological data for a patient related to pain response.

As a second correlation example, FIG. 6 is presented. FIG. 6 includes three graphs that indicate DC levels of various signals. Optical measurement graph 601 includes changes in a DC level over time for a PPG measured using a first optical wavelength ($\lambda_1$), namely signal 610. Optical measurement graph 602 includes changes in a DC level over time for a PPG measured using a second optical wavelength ($\lambda_2$), namely signal 611. Capacitance measurement graph 603 includes changes in a DC level over time for a CPG measured using a capacitive sensor.

In FIG. 6, the three graphs are correlated in time to changes in DC levels, which can be indicative of change in a pain response of a patient. For example, a decrease in the optical DC levels might be primarily due to vasoconstriction of the patient. However, changes in DC levels for a single signal alone might not indicate pain for a patient since various causes of the DC changes might be possible. In FIG. 6, a time wise correlation between PPG measured for two optical wavelengths as well as a CPG is established. For example, a downward trend in the optical PPGs is correlated in time to a downward trend in the CPG signal which can indicate that a changing pain level for the patient. An upward trend in the optical PPGs is not well correlated in time to any changes in DC levels for the CPG which might indicate a non-changing pain level for the patient. Other correlations between PPG and CPG data can be established, such as that found in FIG. 7.

Figure 7:
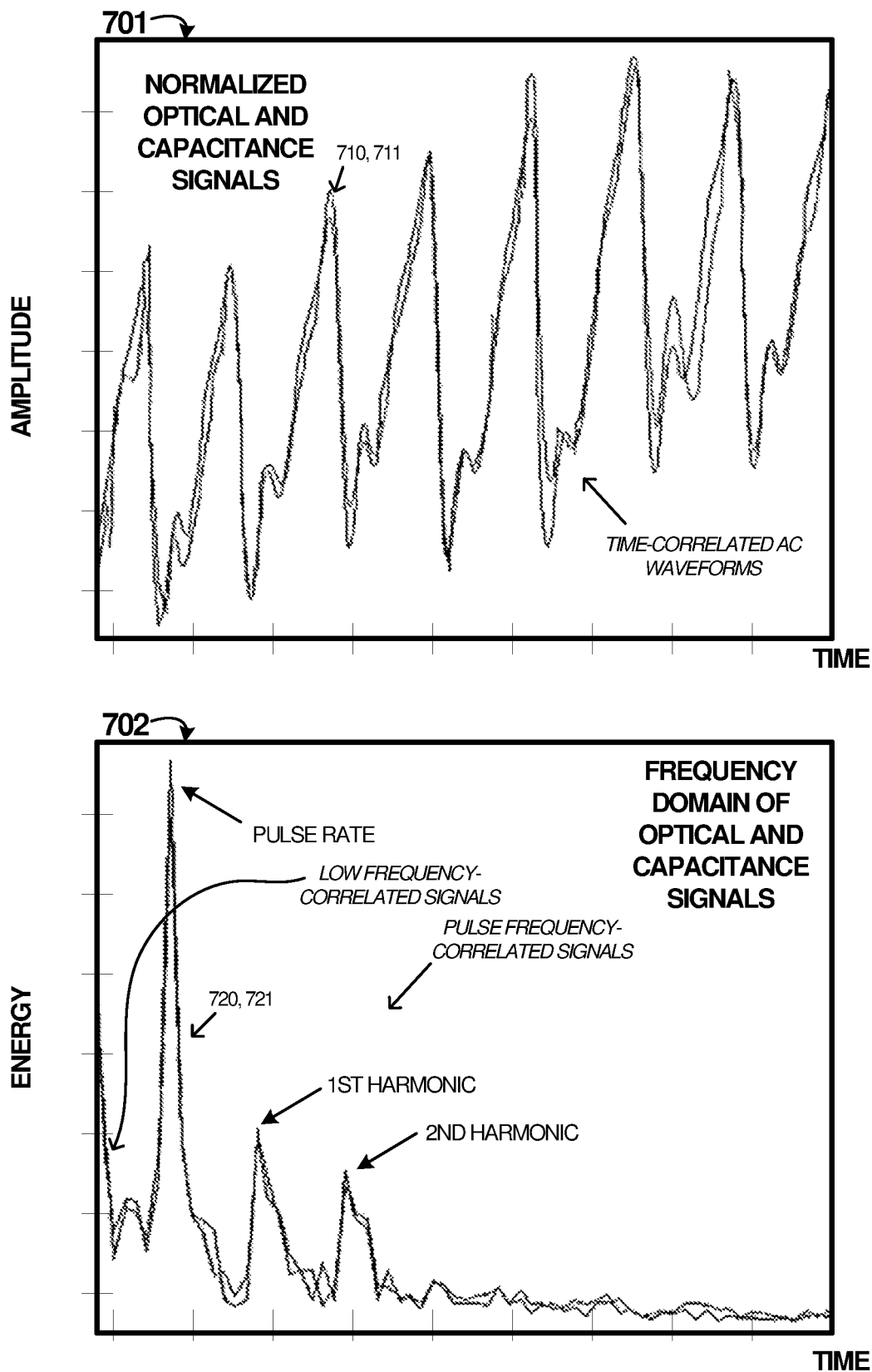
FIG. 7 illustrates measured physiological data for a patient related to pain response.

As a third correlation example, FIG. 7 is presented. FIG. 7 indicates two graphs of further measurements using optical and capacitive sensors. Specifically, graph 701 indicates time-correlated AC waveforms for PPG signal 710 and CPG signal 711. A strong correlation between these two waveforms can indicate that pain response metrics for one signal also qualifies pain response in the other signal as valid. Furthermore, a DC shift in both signals can be seen in graph 701, which can also indicate a pain response, as discussed above for FIGS. 5 and 6.

Graph 702 of FIG. 7 is a frequency-domain graph for PPG 720 and CPG 721. Graph 702 shows correlation in the frequency domain for PPG 720 and CPG 721. In graph 702, a pulse rate is shown by a fundamental frequency of the pulse and upper harmonics. PPG 720 and CPG 721 are well correlated for the pulse signal, and this can indicate that both signals are measuring the patient well. Pain metrics that are identified for CPG 721 can have a higher confidence due to the close correlation to PPG 720. Furthermore, changes in low-frequency content of both signals can be correlated to identify pain responses in the patient. For example, a histogram plot of frequency-domain content can be maintained which can be used to indicate pain response in the patient. If PPG 720 and CPG 721 were not correlated in the frequency domain, then no pain response might be occurring in the patient. Other correlations between PPG and CPG frequency data can be established, as discussed above.

Measurement system 310 reports (406) pain response to an operator. As discussed above, the various signal changes, rates of change, and correlations between signals monitored for the patient can all factor into a pain response of the patient. This pain response can be quantified into an index or other quantity which can be presented to an operator, such as a health care professional monitoring the patient. For example, during a surgical procedure a patient might be placed under anesthesia, but the attending personnel might desire to monitor a level of pain experienced by the patient even though the patient might be unconscious. The pain calibration test performed before unconsciousness can establish baseline patient response to stimuli. This baseline patient response can be analyzed against currently monitored signals, such as capacitance signals, optical signals, or other signals, which might indicate that the patient is experiencing pain even if unconscious. This pain level can drive different medical decisions or guide a surgical procedure to provide the best level of care for the patient.

Figure 8:
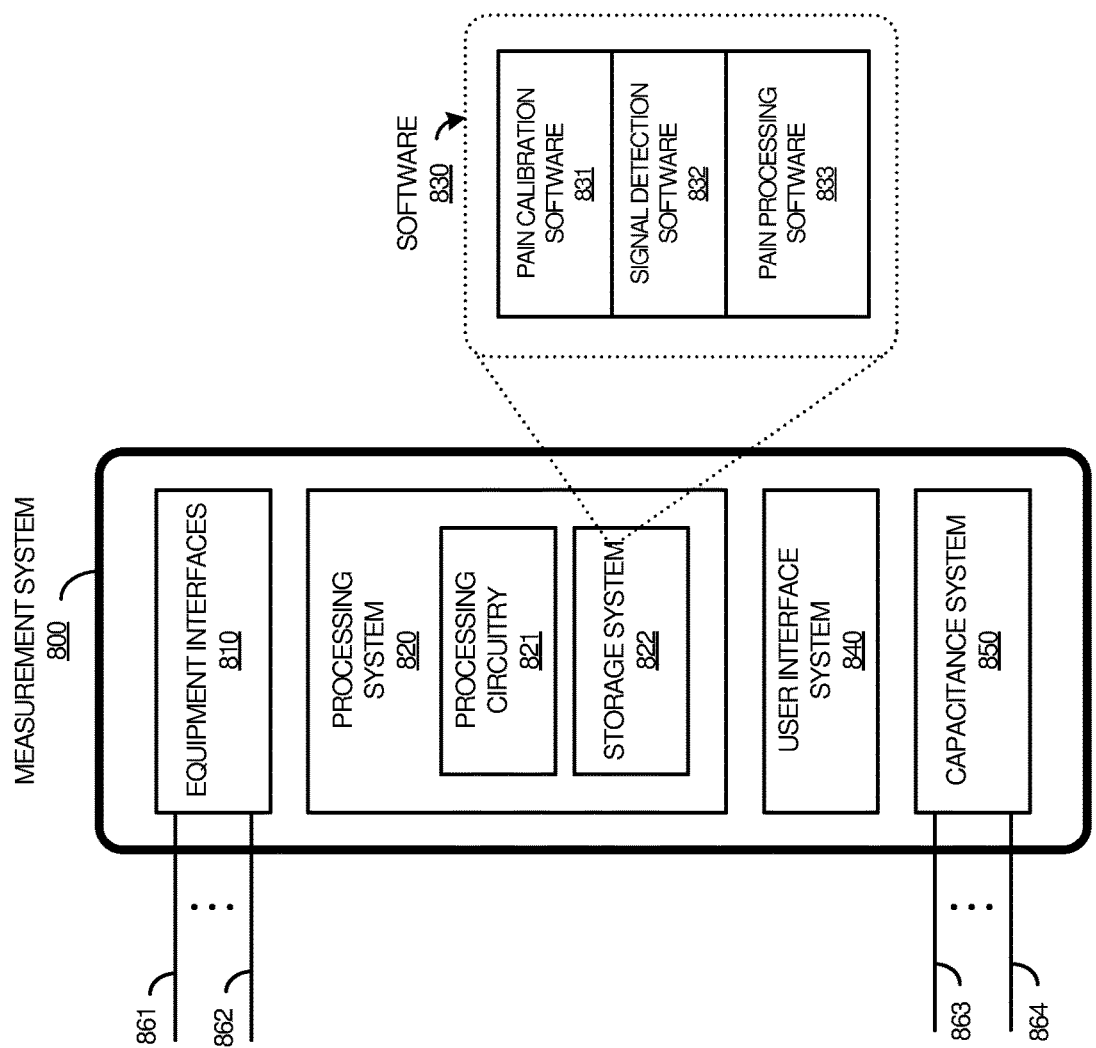
FIG. 8 is a block diagram illustrating a measurement system.

FIG. 8 is a block diagram illustrating measurement system 800, as an example of elements of pain measurement system 110 in FIG. 1 or measurement system 310 in FIG. 3, although these can use other configurations. Measurement system 800 includes equipment interfaces 810, processing system 820, software 830, user interface 840, and capacitance system 850. Processing system 820 further includes processing circuitry 821 and storage system 822. In operation, processing circuitry 821 is operatively linked to equipment interfaces 810, user interface 840, and capacitance system 850 by one or more communication interfaces, which can comprise a bus, discrete connections, network links, software interfaces, or other circuitry. Measurement system 800 can be distributed or consolidated among equipment or circuitry that together forms the elements of measurement system 800. Measurement system 800 can optionally include additional devices, features, or functionality not discussed here for purposes of brevity.

Equipment interfaces 810 comprise one or more communication interfaces for communicating with other circuitry and equipment, such as with patient monitor 115 of FIG. 1, or the various sensor monitors of FIG. 3. Equipment interfaces 810 can include transceiver equipment exchanging communications over one or more of the associated links 861-862. It should be understood that equipment interfaces 810 can include multiple interfaces, pins, transceivers, or other elements for communicating with multiple external devices. Equipment interfaces 810 also receives command and control information and instructions from processing system 820 or user interface 840 for controlling the operations of equipment interfaces 810. Links 861-862 can each use various protocols or communication formats as described herein for links 113-114 of FIG. 1 or links 315-317 of FIG. 3, including combinations, variations, or improvements thereof.

Processing system 820 includes processing circuitry 821 and storage system 822. Processing circuitry 821 retrieves and executes software 830 from storage system 822. In some examples, processing circuitry 821 is located within the same equipment in which equipment interfaces 810, user interface 840, or capacitance system 850 are located. In further examples, processing circuitry 821 comprises specialized circuitry, and software 830 or storage system 822 can be included in the specialized circuitry to operate processing circuitry 821 as described herein. Storage system 822 can include a non-transitory computer-readable medium such as a disk, tape, integrated circuit, server, flash memory, or some other memory device, and also may be distributed among multiple memory devices.

Software 830 may include an operating system, logs, utilities, drivers, networking software, tables, databases, data structures, and other software typically loaded onto a computer system. Software 830 can contain application programs, server software, firmware, processing algorithms, or some other form of computer-readable processing instructions. When executed by processing circuitry 821, software 830 directs processing circuitry 821 to operate as described herein, such as instruct optical or capacitance systems to generate optical or electrical signals for measurement of physiological parameters of patients, receive signals representative of optical or capacitance measurements of patients, and process at least the received signals to determine physiological parameters of patients, among other operations.

In this example, software 830 includes pain calibration software 831, signal detection software 832, and pain processing software 833. It should be understood that a different configuration can be employed, and individual modules of software 830 can be included in different equipment in measurement system 800. Pain calibration software 831 identifies standardized or normalized pain response data for the patient, or establishes calibration data based on pain calibration stimuli. Pain calibration software 831 can determine one or more pain thresholds based on the pain calibration data which can be used in reporting of pain responses for the patient. Signal detection software 832 handles processing of the various signals monitored using physiological sensors, such as optical sensors, capacitive sensors, or other sensors described herein. Signal detection software 832 manages monitoring of these signals over time and establishment of various AC, DC, and frequency representations of these signals, such as by determining PPG signals, CPG signals, EEG signals, or other data, including combinations thereof. Pain processing software 833 processes the various monitored sensor data and associated signals against the pain thresholds or pain calibration data to identify pain metrics and determine when the pain metrics indicate pain responses for the patient. Pain processing software 833 can also handle pain response reporting with user interface 840.

User interface 840 includes equipment and circuitry to communicate information to a user of measurement system 800, such as alerts, measurement results, and measurement status. Examples of the equipment to communicate information to the user can include displays, indicator lights, lamps, light-emitting diodes, haptic feedback devices, audible signal transducers, speakers, buzzers, alarms, vibration devices, or other indicator equipment, including combinations thereof. The information can include blood parameter information, waveforms, summarized blood parameter information, graphs, charts, processing status, or other information. User interface 840 also includes equipment and circuitry for receiving user input and control, such as for beginning, halting, or changing a measurement process or a calibration process. Examples of the equipment and circuitry for receiving user input and control include push buttons, touch screens, selection knobs, dials, switches, actuators, keys, keyboards, pointer devices, microphones, transducers, potentiometers, non-contact sensing circuitry, or other human-interface equipment.

Capacitance system 850 comprises a communication interface for communicating with other circuitry and equipment, such as with capacitance system 112 of FIG. 1 or capacitance monitor 312 of FIG. 3. Capacitance system 850 can include transceiver equipment exchanging communications over one or more of the associated links 863-864. It should be understood that capacitance system 850 can include multiple interfaces, pins, transceivers, or other elements for communicating with multiple external devices. Capacitance system 850 also receives command and control information and instructions from processing system 850 or user interface 840 for controlling the operations of capacitance system 850. Links 863-864 can each use various protocols or communication formats as described herein for links 113 and 140-142 of FIG. 1, or links 315 and 350-351 of FIG. 3, including combinations, variations, or improvements thereof. In some examples, capacitance system 810 includes capacitance interface equipment, such as that discussed above for capacitance system 112 of FIG. 1 or capacitance monitor 312 of FIG. 3.

The included descriptions and drawings depict specific embodiments to teach those skilled in the art how to make and use the best mode. For the purpose of teaching inventive principles, some conventional aspects have been simplified or omitted. Those skilled in the art will appreciate variations from these embodiments that fall within the scope of the invention. Those skilled in the art will also appreciate that the features described above can be combined in various ways to form multiple embodiments. As a result, the invention is not limited to the specific embodiments described above.

What is claimed is:

1. A measurement system to detect pain response in a patient, the measurement system comprising:
    one or more patient sensors, applied to the tissue of the patient;
    a capacitive system configured to measure a capacitance signal for the tissue of the patient, the capacitance signal being a measure of capacitance changing over time, using at least one of the one or more patient sensors;
    a patient monitor configured to measure an electrical signal representing brain activity of the patient, using at least one of the one or more patient sensors; and
    a processing system configured to correlate the capacitance signal and the electrical signal to determine pain metrics, and determine a pain response of the patient based at least on the pain metrics and pain calibration information for the patient.

2. The measurement system of claim 1, wherein the capacitive system is configured to measure the capacitance signal with one or more capacitor plates in the one or more patient sensors.

3. The measurement system of claim 1, wherein the one or more patient sensors are applied to the tissue of the patient.

4. The measurement system of claim 1, wherein the processing system is configured to determine the pain response by at least correlating the pain metrics to further pain metrics identified for the patient that are derived from at least one of a respiration rate, heart rate, electroencephalogram (EEG) data, and photoplethysmogram (PPG) data.

5. The measurement system of claim 1, wherein the pain calibration information comprises capacitance measurements of the patient during one or more calibration stimuli.

6. A measurement system to detect pain response in a patient, the measurement system comprising:
    one or more patient sensors, applied to the tissue of the patient;
    a capacitive system configured to measure a capacitance signal for the tissue of the patient, the capacitance signal being a measure of capacitance changing over time, using at least one of the one or more patient sensors;
    a patient monitor configured to measure an electrical signal representing brain activity of the patient, using at least one of the one or more patient sensors; and
    a processing system configured to determine pain metrics at least in part from a time segment of the capacitance signal and the electrical signal, wherein the pain metrics are determined based on direct current (DC) trends in ones of the capacitance signal and the electrical signal, and determine a pain response of the patient based at least on the pain metrics and pain calibration information for the patient.

7. A measurement system to detect pain response in a patient, the measurement system comprising:
    one or more patient sensors, applied to the tissue of the patient;
    a capacitive system configured to measure a capacitance signal for the tissue of the patient, the capacitance signal being a measure of capacitance changing over time, using at least one of the one or more patient sensors;
    a patient monitor configured to measure an electrical signal representing brain activity of the patient, using at least one of the one or more patient sensors; and
    a processing system configured to determine pain metrics at least in part from a time segment of the capacitance signal and the electrical signal, wherein the pain metrics comprise percentage modulation (PMOD) changes of the capacitance signal that are identified based at least on oscillation amplitude relative to baseline amplitude of the capacitance signal, and determine a pain response of the patient based at least on the pain metrics and pain calibration information for the patient.

8. A measurement system to detect pain response in a patient, the measurement system comprising:
    one or more patient sensors, applied to the tissue of the patient;
    a capacitive system configured to measure a capacitance signal for the tissue of the patient, the capacitance signal being a measure of capacitance changing over time, using at least one of the one or more patient sensors;

a patient monitor configured to measure an electrical signal representing brain activity of the patient, using at least one of the one or more patient sensors; and a processing system configured to determine pain metrics at least in part from a time segment of the capacitance signal and the electrical signal, and determine a pain response of the patient based at least on the pain metrics and pain calibration information for the patient, wherein the pain response is determined by correlating the pain metrics to vasoconstriction metrics derived from plethysmograph data of the patient.

9. A measurement system to detect pain response in a patient, the measurement system comprising:

one or more patient sensors, applied to the tissue of the patient;

a capacitive system configured to measure a capacitance signal for the tissue of the patient, the capacitance signal being a measure of capacitance changing over time, using at least one of the one or more patient sensors, wherein the capacitance signals comprise a capacitance plethysmogram (CPG);

a patient monitor configured to measure an electrical signal representing brain activity of the patient, using at least one of the one or more patient sensors; and a processing system configured to determine pain metrics at least in part from a time segment of the capacitance signal and the electrical signal, and determine a pain response of the patient based at least on the pain metrics and pain calibration information for the patient by correlating frequency components of the CPG to frequency components of a photoplethysmogram (PPG) of the patient.

10. A method of operating a measurement system to detect pain response in a patient, the method comprising:

measuring a capacitance signal for tissue of the patient using a capacitive sensor applied to the tissue of the patient, the capacitance signal being a measure of capacitance changing over time;

measuring an electrical signal representing brain activity of the patient; and determining a pain response of the patient at least in part from pain metrics derived by correlating the capacitance signal and the electrical signal, and pain calibration information for the patient.

11. The method of claim 10, wherein the capacitive sensor comprises one or more capacitor plates arranged on the tissue of the patient.

12. The method of claim 10, further comprising:

determining the pain metrics based on direct current (DC) trends in ones of the capacitance signal and the electrical signal.

13. The method of claim 10, wherein determining the pain response comprises correlating the pain metrics to further pain metrics identified for the patient that are derived from at least one of a respiration rate, heart rate, electroencephalogram (EEG) data, and photoplethysmogram (PPG) data.

14. The method of claim 10, wherein measuring an electrical signal representing brain activity of the patient comprises using at least one brain activity sensor proximate to the tissue of the patient.

15. The method of claim 10, wherein the pain metrics comprise percentage modulation (PMOD) changes of the capacitance signal that are identified based at least on oscillation amplitude relative to baseline amplitude of the capacitance signal.

16. The method of claim 10, wherein determining the pain response comprises correlating the pain metrics to vasoconstriction metrics derived from plethysmograph data of the patient.

17. The method of claim 10, wherein the capacitance signals comprise a capacitance plethysmogram (CPG); and wherein determining the pain response comprises correlating frequency components of the CPG to frequency components of a photoplethysmogram (PPG) of the patient.

18. The method of claim 10, wherein the pain calibration information comprises capacitance measurements of the patient during one or more calibration stimuli.

19. An apparatus comprising:

one or more computer readable storage media; and program instructions stored on the one or more computer readable storage media for at least identifying a pain response in a patient, that when executed by a processing system, direct the processing system to at least:

monitor a capacitance signal for tissue of the patient using at least one capacitor element applied to the tissue of the patient, the capacitance signal being a measure of capacitance changing over time;

process the capacitance signal to derive one or more capacitive pain metrics for the patient;

identify an electrical signal representing brain activity of the patient using at least a brain activity sensor applied to the tissue of the patient;

determine the pain response of the patient based at least on correlating the electrical signal to the capacitive pain metrics.

20. The apparatus of claim 19, wherein the processing instructions further direct the processing system to:

calibrate the pain response of the patient using at least a predetermined pain stimulus calibration to establish at least one pain response threshold; and report an indication of the pain response when the pain response rises above the at least one pain response threshold.

* * * * *